United States Patent
Jiang et al.

(10) Patent No.: US 9,802,876 B2
(45) Date of Patent: Oct. 31, 2017

(54) ALKYLATING PROCESS FOR ALKYL BENZENES

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Jian Jiang, Shanghai (CN); Changxi Miao, Shanghai (CN); Dongyu Jiang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 14/397,706

(22) PCT Filed: Jul. 4, 2013

(86) PCT No.: PCT/CN2013/000817
§ 371 (c)(1),
(2) Date: Oct. 29, 2014

(87) PCT Pub. No.: WO2014/023079
PCT Pub. Date: Feb. 13, 2014

(65) Prior Publication Data
US 2015/0119618 A1    Apr. 30, 2015

(30) Foreign Application Priority Data

Jul. 12, 2012 (CN) .......................... 2012 1 0240056
Sep. 5, 2012 (CN) .......................... 2012 1 0325048

(51) Int. Cl.
C07C 2/86 (2006.01)
B01J 29/14 (2006.01)
C10G 29/20 (2006.01)

(52) U.S. Cl.
CPC ............. *C07C 2/864* (2013.01); *B01J 29/143* (2013.01); *B01J 29/146* (2013.01); *C07C 2/865* (2013.01);
(Continued)

(58) Field of Classification Search
CPC ......... C07C 2/865; C07C 2/867; C07C 2/864; C07C 15/073; C07C 15/46; B01J 29/143; B01J 29/146; C10G 29/205
(Continued)

(56) References Cited

U.S. PATENT DOCUMENTS 4,463,204 A    7/1984 Liu
4,483,936 A    11/1984 Llu et al.
(Continued)

FOREIGN PATENT DOCUMENTS

CN    1326430 A    12/2001
CN    101623649 A    1/2010
(Continued)

OTHER PUBLICATIONS

CN102372549A Translation.*
(Continued)

*Primary Examiner* — Jason Chong
(74) *Attorney, Agent, or Firm* — Buchanan Ingersoll & Rooney PC

(57) ABSTRACT

This invention relates to an alkylating process for alkyl benzenes, including the steps of: a) an alkyl benzene and a first stream of alkylating agent being fed into a first reaction zone, contacting with a catalyst A, to produce a process stream I; b) the process stream I and a second stream of
(Continued)

Figure 1:
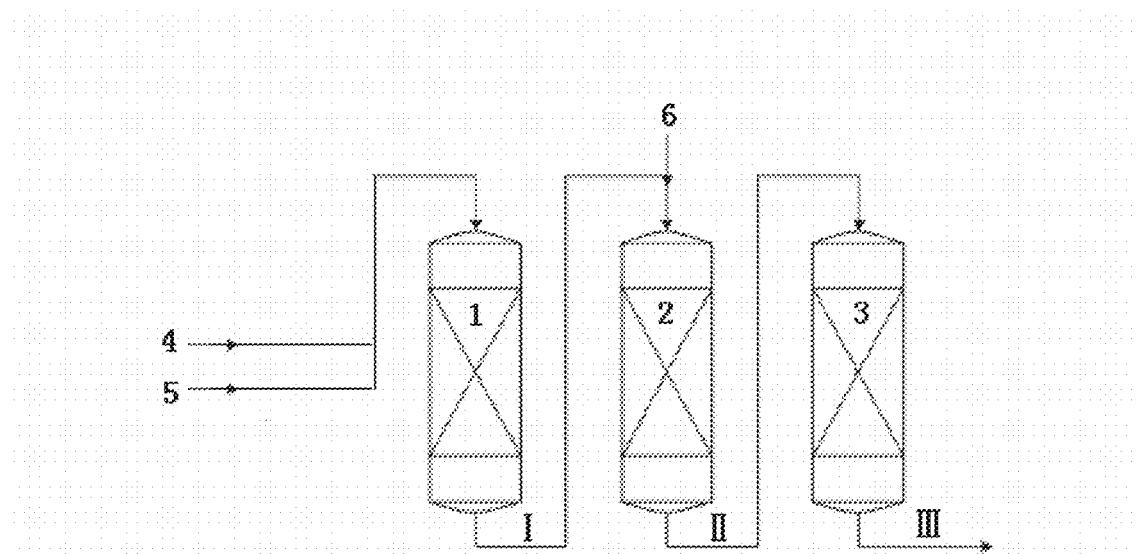

alkylating agent being fed into at least one second reaction zone, contacting with a catalyst B, to produce a process stream II; and c) the process stream II being fed into at least one third reaction zone, contacting with a catalyst C, to produce a process stream III containing an alkylate. The present alkylating process can improve the utilization efficiency of the alkylating agent.

19 Claims, 1 Drawing Sheet

(52) U.S. Cl.
CPC .............. *C07C 2/867* (2013.01); *C10G 29/205* (2013.01); *C07C 2529/08* (2013.01); *C10G 2300/1096* (2013.01); *C10G 2400/30* (2013.01)

(58) Field of Classification Search
USPC .......................................... 585/435, 447, 449
See application file for complete search history.

(56) References Cited

U.S. PATENT DOCUMENTS

| | | | |
|---|---|---|---|
| 6,642,426 B1 | 11/2003 | Johnson et al. | |
| 2009/0253949 A1* | 10/2009 | Ghosh | B01J 29/06 585/454 |
| 2010/0168486 A1 | 7/2010 | Butler et al. | |
| 2011/0196182 A1 | 8/2011 | Thorman | |
| 2012/0296139 A1* | 11/2012 | Pelati | C07C 2/864 585/437 |
| 2013/0011893 A1 | 1/2013 | Mantegazza et al. | |

FOREIGN PATENT DOCUMENTS

| | | | |
|---|---|---|---|
| CN | 101992082 A | 3/2011 | |
| CN | 102040457 A | 5/2011 | |
| CN | 102372549 A1 * | 3/2012 | ........... C07C 15/073 |
| CN | 102040457 B | 4/2014 | |
| CN | 102372549 B | 7/2014 | |
| EA | 201170852 A1 | 1/2012 | |
| WO | WO 2011/077240 A1 | 6/2011 | |
| WO | WO 2011/097096 A1 | 8/2011 | |

OTHER PUBLICATIONS

Office Action dated Dec. 16, 2014, issued by the Chinese Patent Office in corresponding Chinese Patent Application No. 201210325048.0. (4 pages).
International Search Report (PCT/ISA/210) dated Oct. 10, 2013, by the China Patent Office as the International Searching Authority for International Application No. PCT/CN2013/000817.
Office Action dated Sep. 25, 2014, by the Chinese Patent Office in corresponding Chinese Patent Application No. 201210240056.5. (5 pages).
Office Action issued on Mar. 14, 2017, by the Russian Federal Service for Intellectual Property in corresponding Russian Patent Application No. 2014143113 and a partial English Translation of the Office Action. (8 pages).
Notice of Allowance dated May 23, 2017 by the Russian Federal Service for Intellectual Property in corresponding Russian Application No. 2014143113. (11 pages).

* cited by examiner

ALKYLATING PROCESS FOR ALKYL BENZENES

TECHNICAL FIELD

This invention relates to an alkylating process, especially relates to an alkylating process for alkyl benzenes.

BACKGROUND ART

Alkyl styrenes, including styrene, are important starting materials for organic chemical industry, mainly used for producing polystyrenes, ABS resins, SBR rubbers, and unsaturated resins. Up to now, styrene based resins rank worldwide only after PEs and PVCs in terms of production.

The conventional process for producing styrene involves dehydrogenating ethyl benzene, which is a greatly endothermic reaction and requires a great input of heat energy, leading to a reaction temperature of more than 600 degrees centigrade. In view of this, the prior art has developed a process wherein (alkyl) styrenes are directly synthesized by alkylating alkyl benzenes (e.g. toluene) on the side chain in the presence of an alkaline catalyst with an alkylating agent (e.g. methanol), which has been identified as a promising production process due to low cost, low consumption of energy, little environmental pollution, simple procedure and easy availability of the starting materials, and drawn more and more attention. Chinese application No. CN200910201632.3 discloses a process for producing ethyl benzene and styrene by alkylating toluene by methanol on the side chain, wherein the catalyst to be used, by weight, includes 60-99% of a mesoporous carbon carrier, and supported thereon, 0.1-30% of an oxide of alkali metal or alkali earth metal and 0.1-10% of a boron oxide. Chinese application No. CN201010261714.X discloses a process for producing ethyl benzene and styrene by alkylating toluene with methanol on the side chain, wherein the catalyst is ion-exchanged by a K salt before use.

In the alkylating process, toluene and methanol react mainly through the following two routes in the presence of an alkaline catalyst.

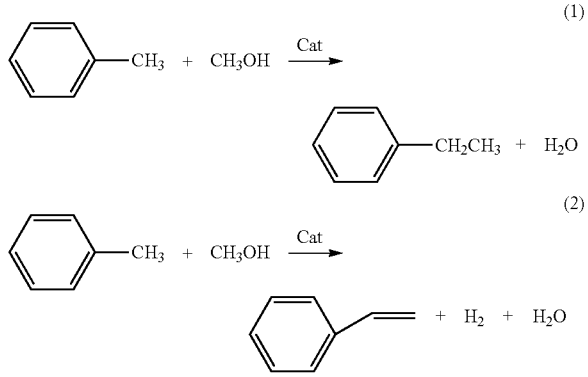

In the presence of the alkaline catalyst, toluene reacts mainly in line with the routes (1) and (2), and at the same, a very minor amount of co-product like xylene or methyl ethyl benzene is produced. However, under this reaction condition, methanol per se will decompose into CO and $H_2$, as illustrated by the following route (3):

From the standpoint of economical value, it is required that as much as possible methanol be converted into ethyl benzene and styrene by reacting with toluene, rather than unnecessarily consumed by this decomposition. When other alkyl benzenes or alkylating agents (e.g. dimethoxy methane) are to be used for the alkylating process, there is a similar concern.

Therefore, there still exists in the prior art a need for an alkylating process for alkyl benzenes, which is capable of effectively inhibiting decomposition of the alkylating agent (especially methanol), whereby improving the utilization efficiency of the alkylating agent.

SUMMARY OF THE INVENTION

Upon in-depth study of the prior art, the present inventors found that the utilization efficiency of the alkylating agent can be improved over that of the prior art if a specific reaction step is involved in the alkylating process, whereby achieving this invention.

Specifically, this invention relates to the following aspects.

1. An alkylating process for alkyl benzenes, including the following steps:

a) an alkyl benzene having the following formula (I) and a first stream of alkylating agent being fed into a first reaction zone, contacting with a catalyst A, to produce a process stream I, wherein the alkylating agent is at least one selected from the group consisting of methanol, formaldehyde and dimethoxy methane,

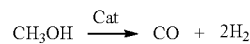

wherein, Rs may be the same as or different from one another, each independently selected from the group consisting of $C_{1-4}$ linear or branched alkyls, preferably methyl, the value n represents the number of the substituent R and is an integer of 0, 1 or 2, preferably 0;

b) the process stream I and a second stream of alkylating agent being fed into at least one second reaction zone, contacting with a catalyst B, to produce a process stream II; and c) the process stream II being fed into at least one third reaction zone, contacting with a catalyst C, to produce a process stream III containing an alkylate.

2. The alkylating process according to any of the proceeding aspects, wherein in the first reaction zone, the reaction temperature is 320-400 degrees centigrade, preferably 380-400 degrees centigrade, the weight hourly space velocity (WHSV) is 2-4 $h^{-1}$, the reaction pressure is 0-0.5 MPa (gage pressure); in the second reaction zone, the reaction temperature is 380-420 degrees centigrade, preferably 395-415 degrees centigrade, the weight hourly space velocity (WHSV) is 2-4 $h^{-1}$, the reaction pressure is 0-0.5

MPa (gage pressure); in the third reaction zone, the reaction temperature is 400-450 degrees centigrade, preferably 400-420 degrees centigrade, the weight hourly space velocity (WHSV) is 2-4 h$^{-1}$, the reaction pressure is 0-0.5 MPa (gage pressure); the ratio by molar of the alkyl benzene to the first stream of alkylating agent is greater than 1 but not greater than 6, preferably 3.5-5.5, and the ratio by molar of the alkyl benzene contained in the process stream I to the second stream of alkylating agent is 1-5, preferably 3-5.

3. The alkylating process according to any of the proceeding aspects, wherein the reaction temperature in the first reaction zone is less than the reaction temperature in the third reaction zone.

4. The alkylating process according to any of the proceeding aspects, wherein the ratio by molar of the alkyl benzene to the first stream of alkylating agent is greater than the ratio by molar of the alkyl benzene contained in the process stream I to the second stream of alkylating agent.

5. The alkylating process according to any of the proceeding aspects, wherein said at least one second reaction zone includes one fixed-bed reactor or two to five serially-connected fixed-bed reactors, said at least one third reaction zone includes one fixed-bed reactor or two to five serially-connected fixed-bed reactors.

6. The alkylating process according to any of the proceeding aspects, wherein at least one of the catalyst A, the catalyst B and the catalyst C is an alkali metal ion exchanged molecular sieve, wherein the molecular sieve is one or more selected from the group consisting of a X molecular sieve and a Y molecular sieve, preferably selected from the group consisting of a X molecular sieve having a SiO$_2$/Al$_2$O$_3$ of 1-7 and a Y molecular sieve having a SiO$_2$/Al$_2$O$_3$ of 1-7, more preferably a X molecular sieve having a SiO$_2$/Al$_2$O$_3$ of 2-3, the alkali metal is selected from a combination of K/Rb (preferably, K and Rb are contained in the catalyst with a content of 0.4-0.8 mmol/g and 2.5-3.1 mmol/g respectively, more preferably K: 0.5-0.7 mmol/g, Rb: 2.8-3.0 mmol/g), a combination of K/Cs (preferably, K and Cs are contained in the catalyst with a content of 0.7-1.3 mmol/g and 1.8-2.5 mmol/g respectively, more preferably K: 0.8-1.2 mmol/g, Cs: 2.0-2.3 mmol/g), a combination of Rb/Cs (preferably, Rb and Cs are contained in the catalyst with a content of 0.8-1.5 mmol/g and 1.0-1.7 mmol/g respectively, more preferably Rb: 1.1-1.4 mmol/g, Cs: 1.3-1.5 mmol/g) or a combination of K/Rb/Cs (preferably, K, Rb and Cs are contained in the catalyst with a content of 0.4-0.9 mmol/g, 0.5-1.0 mmol/g and 1.8-2.5 mmol/g respectively, more preferably K: 0.5-0.7 mmol/g, Rb: 0.6-0.8 mmol/g, Cs: 2.0-2.4 mmol/g), more preferably a combination of K/Rb/Cs (preferably, K, Rb and Cs are contained in the catalyst with a content of 0.5-0.7 mmol/g, 0.6-0.8 mmol/g and 2.0-2.4 mmol/g respectively, more preferably K: 0.6-0.7 mmol/g, Rb: 0.7-0.8 mmol/g, Cs: 2.1-2.3 mmol/g).

7. The alkylating process according to any of the proceeding aspects, wherein at least one of the catalyst A, the catalyst B and the catalyst C is the alkali metal ion exchanged molecular sieve produced in line with a process including the step of contacting a molecular sieve with an alkali metal ion source to conduct ion-exchanging, wherein the molecular sieve is one or more selected from the group consisting of a X molecular sieve and a Y molecular sieve, preferably one or more selected from the group consisting of a X molecular sieve having a SiO$_2$/Al$_2$O$_3$ of 1-7 and a Y molecular sieve having a SiO$_2$/Al$_2$O$_3$ of 1-7, more preferably a X molecular sieve having a SiO$_2$/Al$_2$O$_3$ of 2-3, the alkali metal is selected from a combination of K/Rb (preferably, K and Rb are contained in the catalyst with a content of 0.4-0.8 mmol/g and 2.5-3.1 mmol/g respectively, more preferably K: 0.5-0.7 mmol/g, Rb: 2.8-3.0 mmol/g), a combination of K/Cs (preferably, K and Cs are contained in the catalyst with a content of 0.7-1.3 mmol/g and 1.8-2.5 mmol/g respectively, more preferably K: 0.8-1.2 mmol/g, Cs: 2.0-2.3 mmol/g), a combination of Rb/Cs (preferably, Rb and Cs are contained in the catalyst with a content of 0.8-1.5 mmol/g and 1.0-1.7 mmol/g respectively, more preferably Rb: 1.1-1.4 mmol/g, Cs: 1.3-1.5 mmol/g) or a combination of K/Rb/Cs (preferably, K, Rb and Cs are contained in the catalyst with a content of 0.4-0.9 mmol/g, 0.5-1.0 mmol/g and 1.8-2.5 mmol/g respectively, more preferably K: 0.5-0.7 mmol/g, Rb: 0.6-0.8 mmol/g, Cs: 2.0-2.4 mmol/g), more preferably a combination of K/Rb/Cs (preferably, K, Rb and Cs are contained in the catalyst with a content of 0.5-0.7 mmol/g, 0.6-0.8 mmol/g and 2.0-2.4 mmol/g respectively, more preferably K: 0.6-0.7 mmol/g, Rb: 0.7-0.8 mmol/g, Cs: 2.1-2.3 mmol/g).

8. The alkylating process according to any of the proceeding aspects, wherein the alkali metal is the combination of K/Rb/Cs (preferably, K, Rb and Cs are contained in the catalyst with a content of 0.5-0.7 mmol/g, 0.6-0.8 mmol/g and 2.0-2.4 mmol/g respectively, more preferably K: 0.6-0.7 mmol/g, Rb: 0.7-0.8 mmol/g, Cs: 2.1-2.3 mmol/g), and the contacting includes bringing the molecular sieve into contact with a K ion source, a Rb ion source and a Cs ion source sequentially.

9. The alkylating process according to any of the proceeding aspects, further including the following steps:
d) condensing the process stream III, to obtain a process stream IV, and a vapor stream V containing CO and H$_2$;
e) separating the process stream IV, to obtain an aqueous phase stream and an oil phase stream VI; and
f) separating the oil phase stream VI, to obtain an alkyl benzene and the alkylate.

10. The alkylating process according to any of the proceeding aspects, wherein the alkyl benzene obtained from the step f) is recycled to the step a) and/or the step b).

Technical Effect

According to the alkylating process of this invention, the decomposition of the alkylating agent (especially methanol) can be effectively inhibited, whereby significantly improving the utilization efficiency of the alkylating agent.

According to the alkylating process of this invention, by co-using a specific alkylating catalyst, the utilization efficiency of the alkylating agent can be further improved.

FIGURE DESCRIPTION

FIG. 1 schematically illustrates the alkylating process according to this invention.

Figure 2:
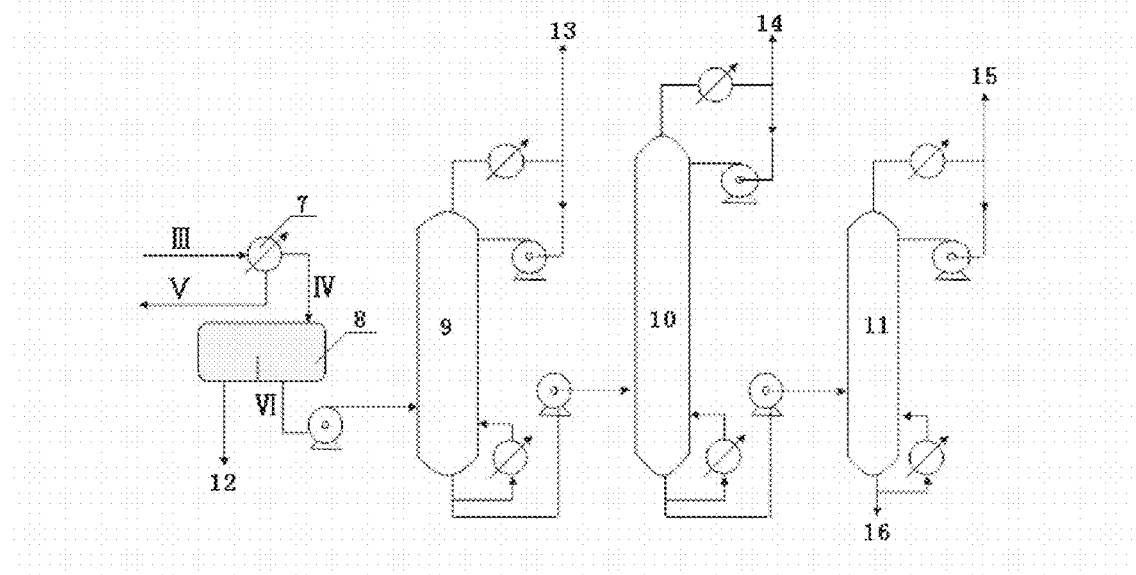

FIG. 2 schematically illustrates the separation and purification step involved in the alkylating process according to this invention.

DETAILED DESCRIPTION OF THE INVENTION

This invention will be described in details hereinafter with reference to the following specific embodiments. However, it is known that the protection scope of this invention should not be construed as limited to these specific embodiments, but rather determined by the attached claims.

In the context of this invention, when an expression like "conventionally known in this field" or "conventionally used in this field" or the like is used to describe/define an item like a material, a process, a part, an apparatus or a device, it means that this item (1) has been well known for a similar purpose in this field before this application, or (2) was not that much well known for a similar purpose in this field before this application but got well known for a similar purpose in this field after this application.

In the context of this invention, unless otherwise specifically mentioned, any percentages, parts and ratios are on a weight basis.

According to this invention, disclosed is an alkylating process for alkyl benzenes, including the following steps:
a) an alkyl benzene and a first stream of alkylating agent as the starting materials being fed into a first reaction zone, contacting with a catalyst A, to produce a process stream I,
b) the process stream I and a second stream of alkylating agent being fed into at least one second reaction zone, contacting with a catalyst B, to produce a process stream II; and
c) the process stream II being fed into at least one third reaction zone, contacting with a catalyst C, to produce a process stream III containing an alkylate.

According to this invention, the alkyl benzene is represented by the following formula (I).

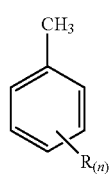

(I)

In the formula, Rs may be the same as or different from one another, each independently selected from the group consisting of $C_{1-4}$ linear or branched alkyls, preferably methyl. The value n represents the number of the substituent R, and is an integer of 0, 1 or 2, preferably 0.

According to this invention, there is no specific limitation as to the position (i.e. the position with respect to methyl illustrated in the formula (I)) of the substituent R (if present) on the benzene ring. For example, if one R exists, said R may be positioned on a para-position, meta-position or opposite position with respect to methyl, preferably the opposite position. When two Rs exits, said R may be positioned on the 2,3-position, 2,4-position, 2,5-position, 2,6-position, 3,4-position or 3,5-position with respect to methyl.

According to this invention, as the alkyl benzene, more preferably toluene.

According to this invention, the alkyl benzenes could be used with one kind thereof or as a mixture of two or more kinds.

According to this invention, the first stream of alkylating agent and the second stream of alkylating agent may be the same as or different from each other (preferably the same as each other), each independently represents one or more selected from the group consisting of methanol, formaldehyde (e.g. formaldehyde, an aqueous formaldehyde solution, paraformaldehyde or polyformaldehyde) and dimethoxy methane, more preferably methanol.

These alkylating agents could be used with one kind thereof or as a mixture of two or more kinds.

According to this invention, in the first reaction zone, the reaction temperature is generally 320-400 degrees centigrade, preferably 380-400 degrees centigrade.

According to this invention, in the first reaction zone, the weight hourly space velocity (WHSV) is generally 2-4 $h^{-1}$, preferably 2-3.5 $h^{-1}$.

According to this invention, in the first reaction zone, the reaction pressure is generally 0-0.5 MPa (gage pressure), preferably 0-0.3 MPa (gage pressure).

According to this invention, in the second reaction zone, the reaction temperature is generally 380-420 degrees centigrade, preferably 395-415 degrees centigrade.

According to this invention, in the second reaction zone, the weight hourly space velocity (WHSV) is generally 2-4 $h^{-1}$, preferably 2.3-3.6 $h^{-1}$.

According to this invention, in the second reaction zone, the reaction pressure is generally 0-0.5 MPa (gage pressure) preferably 0-0.3 MPa (gage pressure).

According to this invention, in the third reaction zone, the reaction temperature is generally 400-450 degrees centigrade, preferably 400-420 degrees centigrade.

According to this invention, in the third reaction zone, the weight hourly space velocity (WHSV) is generally 2-4 $h^{-1}$, preferably 2.3-3.6 $h^{-1}$.

According to this invention, in the third reaction zone, the reaction pressure is generally 0-0.5 MPa (gage pressure), preferably 0-0.3 MPa (gage pressure).

According to this invention, the ratio by molar of the alkyl benzene to the first stream of alkylating agent is generally greater than 1 but not greater than 6, preferably 3.5-5.5.

According to this invention, to prevent the conversion of alkyl benzenes from significantly decreasing, the ratio is set as greater than 1 (preferably 3.5 or more), that is, greater than the stoichiometric ratio of the alkylating reaction, but normally not greater than 6 (preferably 5.5 or less), whereby effectively inhibiting the thermal decomposition of the alkylating agent in this step a).

According to this invention, the ratio by molar of the alkyl benzene (i.e. the alkyl benzene remained after the first reaction zone, contained in the process stream I) to the second stream of alkylating agent is generally 1-5, preferably 3-5.

According to this invention, it is preferred that, the ratio by molar of the alkyl benzene to the first stream of alkylating agent is greater than the ratio by molar of the alkyl benzene contained in the process stream I to the second stream of alkylating agent; in other words, the amount of the alkylating agent to be used in the step b) is intentionally decreased.

According to this invention, it is preferred that, the reaction temperature in the first reaction zone is less than the reaction temperature in the third reaction zone.

According to this invention, relatively decreasing the temperature in the first reaction zone will facilitate inhibiting the thermal decomposition of the alkylating agent like methanol, relatively increasing the temperature in the third reaction zone will facilitate improving the conversion of alkyl benzenes like toluene.

According to this invention, the first reaction zone, the at least one second reaction zone and the at least one third reaction zone may represent individually independent reactors, or individually independent reaction sections/stages of one single reactor, or a combination thereof.

According to this invention, as the first reaction zone, a fixed-bed reactor, a moving bed reactor or a fluidized-bed reactor could be exemplified, preferably the fixed-bed reactor. As the fixed-bed reactor, one conventionally used in this field for conducting the alkylating process for alkyl benzenes can be used, but without limiting thereto.

According to this invention, at least one (e.g. from 1 to 5) second reaction zone should be used. As the second reaction zone, a fixed-bed reactor, a moving bed reactor or a fluidized-bed reactor could be exemplified, preferably the fixed-bed reactor. When multiple exists, these fixed-bed reactors may be serially connected. As the fixed-bed reactor, one conventionally used in this field for conducting the alkylating process for alkyl benzenes can be used, but without limiting thereto.

According to this invention, at least one (e.g. from 1 to 5) third reaction zone should be used. As the third reaction zone, a fixed-bed reactor, a moving bed reactor or a fluidized-bed reactor could be exemplified, preferably the fixed-bed reactor. When multiple exists, these fixed-bed reactors may be serially connected. As the fixed-bed reactor, one conventionally used in this field for conducting the alkylating process for alkyl benzenes can be used, but without limiting thereto.

According to this invention, there is no specific limitation as to how to feed/or load the starting materials (e.g. the alkyl benzene, the alkylating agent, the process streams I and II, or the catalysts A, B and C) into each reaction zone, and any technology conventionally known in this field for this purpose can be directly used. For this reason, any detailed description thereon is omitted herein.

In the following, description in connection with the figures will be given to further explain the alkylating process according to this invention.

In FIG. 1, the reference number 1 represents the first reaction zone, 2 represents the second reaction zone, 3 represents the third reaction zone, 4 represents alkyl benzene, 5 represents the first stream of alkylating agent, 6 represents the second stream of alkylating agent, wherein the process stream I represents the effluent from the first reaction zone, the process stream II represents the effluent from the second reaction zone, the process stream III represents the effluent from the third reaction zone. Specifically, according to FIG. 1, alkyl benzene 4 and the first stream of alkylating agent 5 are fed into the first reaction zone 1, contact with the catalyst A (not shown), to produce the process stream I. Then, the process stream I and the second stream of alkylating agent 6 are fed into the second reaction zone 2, contact with the catalyst B (not shown), to produce the process stream II. Then, the process stream II is fed into the third reaction zone 3, contact with the catalyst C (not shown), to produce the process stream III containing the alkylate.

According to this invention, as the catalyst A, the catalyst B and the catalyst C, any alkaline alkylating catalyst conventionally used in this field for the alkylating of alkyl benzenes can be used, including but not limiting to those disclosed by Chinese application publication No. CN101623649A or CN101992082A. These alkaline catalysts could be used with one kind thereof or as a mixture of two or more kinds.

According to a preferred embodiment of this invention, at least one of the catalyst A, the catalyst B and the catalyst C is an alkali metal ion exchanged molecular sieve, whereby further improving the utilization efficiency of the alkylating agent.

According to this invention, the molecular sieve is one or more selected from the group consisting of a X molecular sieve and a Y molecular sieve, preferably a X molecular sieve. As the Y molecular sieve, preferably a Y molecular sieve having a $SiO_2/Al_2O_3$ of 1-7. As the X molecular sieve, preferably a X molecular sieve having a $SiO_2/Al_2O_3$ of 1-7, more preferably a X molecular sieve having a $SiO_2/Al_2O_3$ of 2-3.

According to this invention, the alkali metal is selected from a combination of K/Rb (preferably, K and Rb are contained in the catalyst with a content (with respect to 1 g of the catalyst) of 0.4-0.8 mmol/g and 2.5-3.1 mmol/g respectively, more preferably K: 0.5-0.7 mmol/g, Rb: 2.8-3.0 mmol/g), a combination of K/Cs (preferably, K and Cs are contained in the catalyst with a content (with respect to 1 g of the catalyst) of 0.7-1.3 mmol/g and 1.8-2.5 mmol/g respectively, more preferably K: 0.8-1.2 mmol/g, Cs: 2.0-2.3 mmol/g), a combination of Rb/Cs (preferably, Rb and Cs are contained in the catalyst with a content (with respect to 1 g of the catalyst) of 0.8-1.5 mmol/g and 1.0-1.7 mmol/g respectively, more preferably Rb: 1.1-1.4 mmol/g, Cs: 1.3-1.5 mmol/g) or a combination of K/Rb/Cs (preferably, K, Rb and Cs are contained in the catalyst with a content (with respect to 1 g of the catalyst) of 0.4-0.9 mmol/g, 0.5-1.0 mmol/g and 1.8-2.5 mmol/g respectively, more preferably K: 0.5-0.7 mmol/g, Rb: 0.6-0.8 mmol/g, Cs: 2.0-2.4 mmol/g), more preferably a combination of K/Rb/Cs (preferably, K, Rb and Cs are contained in the catalyst with a content (with respect to 1 g of the catalyst) of 0.5-0.7 mmol/g, 0.6-0.8 mmol/g and 2.0-2.4 mmol/g respectively, more preferably K: 0.6-0.7 mmol/g, Rb: 0.7-0.8 mmol/g, Cs: 2.1-2.3 mmol/g).

According to this invention, if needed, the alkali metal ion exchanged molecular sieve may further contain one or more additive(s) selected from the group consisting of alkali earth metals (e.g. Ca, Mg and Ba), La, Ce, Zr, B, P, Cu, Mn, Ag, Fe, and Zn. In general, the total amount of these additives in the alkali metal ion exchanged molecular sieve may be 3 wt % or less (with respect to the total mass of the alkali metal ion exchanged molecular sieve), but not limiting thereto. These additives can be introduced into the alkali metal ion exchanged molecular sieve by any method conventionally known in this field (e.g. that disclosed by Chinese application publication No. CN101623649A or the U.S. Pat. No. 4,483,936).

These alkali metal ion exchanged molecular sieves could be used with one kind thereof or as a mixture of two or more kinds.

According to this invention, the alkali metal ion exchanged molecular sieve could be produced in line with the following process.

According to this invention, the process includes a step of contacting a molecular sieve with an alkali metal ion source to conduct ion-exchanging.

According to this invention, the molecular sieve is one or more selected from the group consisting of a X molecular sieve and a Y molecular sieve, preferably a X molecular sieve. As the Y molecular sieve, a Y molecular sieve having a $SiO_2/Al_2O_3$ of 1-7 could be exemplified. As the X molecular sieve, a X molecular sieve having a $SiO_2/Al_2O_3$ of 1-7 could be exemplified, preferably a X molecular sieve having a $SiO_2/Al_2O_3$ of 2-3. For these molecular sieves, a Na type thereof is generally used.

According to this invention, as the alkali metal ion source, a combination of a K ion source and a Rb ion source, a combination of a K ion source and a Cs ion source, a combination of a Rb ion source and a Cs ion source, and a combination of a K ion source, a Rb ion source and a Cs ion source could be exemplified, preferably the combination of a K ion source, a Rb ion source and a Cs ion source. As the ion source, hydroxides, inorganic acid salts (e.g. halides or nitrates) or organic acid salts (e.g. acetates) of these alkali metals could be exemplified, but not limiting thereto.

According to this invention, there is no specific limitation as to the way of contacting the molecular sieve with the alkali metal ion source to conduct the ion-exchanging, which could be conducted by any way conventionally known in this field.

Specifically, as the way for ion exchanging, a solid ion exchanging method and a liquid ion exchanging method could be exemplified.

According to this invention, as the solid ion exchanging method, a method wherein the molecular sieve and the alkali metal ion source (e.g. halides of alkali metal) are mixed together and ground at the normal temperature or under heat, and optionally further calcinated, could be exemplified.

According to this invention, as the liquid ion exchanging method, a method wherein the molecular sieve and the alkali metal ion source contact with each other in the presence of a solvent so as to conduct the ion exchanging, could be exemplified. As the solvent, water could be exemplified. To this end, as the liquid ion exchanging method, preference is given to a method wherein the molecular sieve contacts with an aqueous solution of the alkali metal ion source to conduct the ion exchanging. Herein, the content of the alkali metal ion (i.e. the K, Rb or Cs ion) in the aqueous solution could be 0.5-2.5 mol/L. According to this invention, the temperature at which the contacting (ion-exchanging) is conducted could be 50-90 degrees centigrade, the time duration could be 1-3 h, and the ratio by weight of the molecular sieve to the aqueous solution for each contacting could be 1:(5-10).

According to this invention, the contacting could be conducted for one or more times, preferably 2-6 times, more preferably 2-4 times, but not limiting thereto, with the only proviso that in the finally obtained alkali metal ion exchanged molecular sieve, each alkali metal is contained with a content as hereinbefore defined.

According to this invention, there is no specific limitation as to the sequence in which the alkali metal ion sources contact with the molecular sieve, but preference is given to the sequence of the K ion source, the Rb ion source and the Cs ion source, one after another from which contact with the molecular sieve. For example, when a combination of a K ion source and a Rb ion source is used, it is preferred that the molecular sieve firstly contacts with the K ion source as aforesaid for one or more times, and then contacts with the Rb ion source as aforesaid for one or more times. When a combination of a K ion source, a Rb ion source and a Cs ion source is used, it is preferred that the molecular sieve firstly contacts with the K ion source as aforesaid for one or more times, and then contacts with the Rb ion source as aforesaid for one or more times, and then contacts with the Cs ion source as aforesaid for one or more times.

According to this invention, upon completion of the ion exchanging, water or other solvent could be removed from the reaction product by a drying method conventionally known in this field, to obtain the alkali metal ion exchanged molecular sieve.

According to this invention, any suitable method conventionally known in this field could be used to separate and purifying the obtained alkylate. For example, a method involving the following steps could be mentioned.

d) condensing the process stream III, e.g. by a condenser, to obtain a process stream IV and a vapor stream V containing CO and $H_2$;

e) separating the process stream IV, e.g. by a phase separator, to obtain an aqueous phase stream and an oil phase stream VI; and f) separating the oil phase stream VI, to obtain an alkyl benzene (i.e. un-reacted starting alkyl benzene) and the alkylate.

According to this invention, the alkylate is a compound having the following formula (II) (hereinafter referred to as product A) and/or a compound having the following formula (III) (hereinafter referred to as product B).

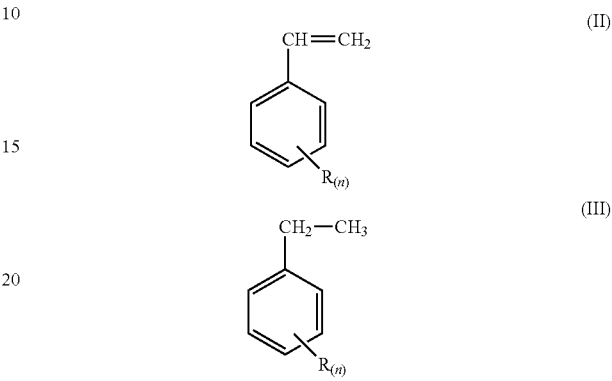

In each formula, R and n are as hereinbefore defined.

According to an embodiment of this invention, the alkyl benzene is toluene, the product A is styrene, the product B is ethyl benzene. To this end, to conduct the step f), as an example, the oil phase stream VI could be sequentially fed into a toluene tower, an ethyl benzene tower and a styrene tower, whereby recovering toluene and purifying ethyl benzene and styrene.

According to this embodiment, the toluene tower may be operated under the condition of a plate number of 30-40, a top temperature of 110-120 degrees centigrade, a top pressure of 165-175 KPa (gage pressure), a bottom temperature of 160-170 degrees centigrade, a bottom pressure of 195-205 KPa (gage pressure), a reflux ratio of 8-13; the ethyl benzene tower may be operated under the condition of a plate number of 90-100, a top temperature of 100-110 degrees centigrade, a top pressure of 35-45 KPa (gage pressure), a bottom temperature of 115-125 degrees centigrade, a bottom pressure of 50-60 KPa (gage pressure), a reflux ratio of 8-13; the styrene tower may be operated under the condition of a plate number of 20-30, a top temperature of 75-85 degrees centigrade, a top pressure of 5-15 KPa (gage pressure), a bottom temperature of 95-105 degrees centigrade, a bottom pressure of 15-25 KPa (gage pressure), a reflux ratio of 1-6.

The separating and purifying will be further explained by referring to the figures.

In FIG. 2, the reference number 7 represents the condenser, 8 represents the phase separator, 9 represents the toluene tower, 10 represents the ethyl benzene tower, 11 represents the styrene tower, 12 represents the aqueous phase, 13 represents toluene, 14 represents ethyl benzene, 15 represents styrene, 16 represents a process stream from the bottom of the styrene tower, wherein the process stream III represents the effluent from the third reaction zone, the process stream IV represents a liquid phase stream obtained from the condenser by condensation, and the process stream V represents a vapor stream obtained from the condenser by condensation. The process stream IV is fed into the phase separator 8, to obtain the aqueous phase stream 12 and the oil phase stream VI. The oil phase stream VI is fed into the toluene tower 9, the ethyl benzene tower 10 and the styrene tower 11 sequentially, to obtain toluene 13, ethyl benzene 14 and styrene 15 respectively. Herein, the effluent from the top of the toluene tower is mainly consisted of toluene and a very minor amount of un-reacted methanol, while ethyl benzene, styrene and other heavier aromatic by-products are discharged from the bottom of the tower. The effluent from the top of the ethyl benzene tower is mainly consisted of ethyl benzene, while that from the bottom of the tower comprises styrene and heavier aromatic by-products. The effluent from the top of the styrene tower is mainly consisted of styrene, while that from the bottom is heavier aromatics.

According to this invention, the alkyl benzene recovered from the step f) could be recycled to the step a) and/or the step b), as a supplementary to the alkyl benzene to be consumed by these steps.

According to this invention, the vapor stream V could be recovered and fired to generate heat energy needed by the reaction; or, via a suitable synthetic apparatus (e.g. that for producing methanol from syngas), be converted into an alkylating agent like methanol, and then recycled.

According to this invention, the utilization efficiency of the alkylating agent and the overall selectivity to alkylate are calculated in line with the following formulae respectively. For an easy description, in this formula, methanol is exemplified as the alkylating agent, toluene is exemplified as the alkyl benzene, and ethyl benzene and styrene are exemplified as the alkylate, however, this invention does not limit to same.

$$\text{Utilization efficiency of methanol} = \frac{\text{Amount by molar of methanol reacted with toluene}}{\text{Amount by molar of methanol fed}} \times 100\%$$

$$\text{Overall selectivity to ethyl benzene/styrene} = \frac{\text{Total amount by molar of ethyl benzene and styrene produced}}{\text{Total amount by molar of aromatics produced}} \times 100\%$$

According to this invention, by feeding the alkylating agent by multiple steps and having same reacted in multiply staged reaction zones, the decomposition of the alkylating agent could be effectively inhibited, whereby significantly improving the utilization efficiency of the alkylating agent. Taking methanol as the example, as compared with the process wherein methanol is fed by one single step and reacted in one staged reaction zone, the process of this invention improves the utilization efficiency of methanol by 5% or more, which is identified as superior in this field.

EXAMPLE

The present invention is further illustrated by using the following examples, but not limiting to same.

Catalyst Preparation Example 1

10 g NaX molecular sieve (having a $SiO_2/Al_2O_3=2.19$) was weighted, at 80 degrees centigrade, in 100 ml KOH solution (1 mol/L), ion-exchanged for 3 times (2 h for each time), then in 50 ml CsOH solution (1 mol/L) for 3 times; after filtered, dried at 100 degrees centigrade for 10 h, to obtain a catalyst C-1.

Catalyst Preparation Example 2

The Catalyst preparation example 1 was repeated except that a NaX molecular sieve having a $SiO_2/Al_2O_3=2.57$ was used instead, to obtain a catalyst C-2.

Catalyst Preparation Example 3

The Catalyst preparation example 1 was repeated except that a NaX molecular sieve having a $SiO_2/Al_2O_3=5.58$ was used instead, to obtain a catalyst C-3.

Catalyst Preparation Example 4

10 g NaX molecular sieve (having a $SiO_2/Al_2O_3=2.19$) was weighted, at 80 degrees centigrade, in 100 ml $KNO_3$ solution (1 mol/L), ion-exchanged for 3 times (2 h for each time); then in 50 ml $CsNO_3$ solution (1 mol/L) for 3 times; after filtered, dried at 100 degrees centigrade for 10 h, to obtain a catalyst C-4.

Catalyst Preparation Example 5

10 g NaX molecular sieve (having a $SiO_2/Al_2O_3=2.19$) was weighted, at 80 degrees centigrade, in 100 ml $KNO_3$ solution (1 mol/L), ion-exchanged for 3 times (2 h for each time); then in 50 ml CsOH solution (1 mol/L) for 3 times; after filtered, dried at 100 degrees centigrade for 10 h, to obtain a catalyst C-5.

Catalyst Preparation Example 6

10 g NaX molecular sieve (having a $SiO_2/Al_2O_3=2.19$) was weighted, at 80 degrees centigrade, in 100 ml KOH solution (1 mol/L), ion-exchanged for 2 times (2 h for each time); then in 50 ml RbOH solution (1 mol/L) for 2 times; finally in 50 ml CsOH solution (1 mol/L) for 2 times; after filtered, dried at 100 degrees centigrade for 10 h, to obtain a catalyst C-6.

Catalyst Preparation Example 7

10 g NaX molecular sieve (having a $SiO_2/Al_2O_3=2.19$) was weighted, at 80 degrees centigrade, in 100 ml KOH solution (1 mol/L), ion-exchanged for 3 times (2 h for each time), after filtered, dried at 100 degrees centigrade for 10 h, to obtain a catalyst C-7.

Catalyst Preparation Example 8

10 g NaX molecular sieve (having a $SiO_2/Al_2O_3=2.19$) was weighted, at 80 degrees centigrade, in 100 ml CsOH solution (1 mol/L), ion-exchanged for 3 times (2 h for each time), after filtered, dried at 100 degrees centigrade for 10 h, to obtain a catalyst C-8.

Application Example 1

Toluene and a first stream of methanol was fed into a first reaction zone, contacted with a catalyst, to produce a first reaction effluent. The first reaction effluent and a second stream of methanol was fed into a second reaction zone, contacted with a catalyst, to produce a second reaction effluent. The second reaction effluent was fed into a third reaction zone, contacted with a catalyst, to produce a third reaction effluent containing ethyl benzene and styrene. From the third reaction effluent, ethyl benzene and styrene were separated.

In this example, the first reaction zone, the second reaction zone and the third reaction zone were all one-staged fixed-bed reactor, loaded with the same catalyst respectively, i.e. one of the catalysts C-1 to C-8. In the first reaction zone, the reaction temperature was 385 degrees centigrade, the weight hourly space velocity (WHSV) was 2.7 $h^{-1}$, the reaction pressure was 0.1 MPa (gage pressure). In the second reaction zone, the reaction temperature was 400 degrees centigrade, the weight hourly space velocity (WHSV) was 3 $h^{-1}$, the reaction pressure was 0.1 MPa (gage pressure). In the third reaction zone, the reaction temperature was 415 degrees centigrade, the weight hourly space velocity (WHSV) was 3 $h^{-1}$, the reaction pressure was 0.1 MPa (gage pressure). The ratio by molar of toluene to the first stream of methanol in the first reaction zone was 5:1, and the ratio by molar of toluene contained in the first reaction effluent to the second stream of methanol was 4:1.

The toluene tower was operated under the condition of a top temperature of 117 degrees centigrade, a top pressure of 172 KPa (gage pressure), a plate number of 35, a bottom temperature of 163 degrees centigrade, a bottom pressure of 200 KPa (gage pressure), a reflux ratio of 12.

The ethyl benzene tower was operated under the condition of a top temperature of 108 degrees centigrade, a top pressure of 45 KPa (gage pressure), a plate number of 95, a bottom temperature of 116 degrees centigrade, a bottom pressure of 58 KPa (gage pressure), a reflux ratio of 12.

The styrene tower was operated under the condition of a top temperature of 85 degrees centigrade, a top pressure of 15 KPa (gage pressure), a plate number of 25, a bottom temperature of 105 degrees centigrade, a bottom pressure of 25 KPa (gage pressure), a reflux ratio of 5.

The reaction was conducted for 20 h. The results were shown in the following Table 1.

TABLE 1

| No. | Catalyst Nos. | utilization efficiency of the alkylating agent, % | overall selectivity to the alkylate, % |
|---|---|---|---|
| 1 | C-1 | 40.2 | 97.5 |
| 2 | C-2 | 32.6 | 98.1 |
| 3 | C-3 | 19.2 | 97.6 |
| 4 | C-4 | 30.1 | 98.0 |
| 5 | C-5 | 32.2 | 97.3 |
| 6 | C-6 | 53.6 | 96.8 |
| 7 | C-7 | 15.1 | 97.4 |
| 8 | C-8 | 16.8 | 97.2 |

Application Example 2

The same as Application example 1, except that each reaction zone was changed with its operation conditions and each reaction zone was loaded with the same catalyst C-1. In the first reaction zone, the reaction temperature was 380 degrees centigrade, the weight hourly space velocity (WHSV) was 2.5 $h^{-1}$, the reaction pressure was 0.15 MPa (gage pressure). In the second reaction zone, the reaction temperature was 400 degrees centigrade, the weight hourly space velocity (WHSV) was 2.9 $h^{-1}$, the reaction pressure was 0.1 MPa (gage pressure). In the third reaction zone, the reaction temperature was 410 degrees centigrade, the weight hourly space velocity (WHSV) was 2.9 $h^{-1}$, the reaction pressure was 0.09 MPa (gage pressure). The ratio by molar of toluene to the first stream of methanol in the first reaction zone was 5:1, and the ratio by molar of toluene contained in the first reaction effluent to the second stream of methanol was 4:1.

The toluene tower was operated under the condition of a top temperature of 115 degrees centigrade, a top pressure of 170 KPa (gage pressure), a plate number of 35, a bottom temperature of 165 degrees centigrade, a bottom pressure of 200 KPa (gage pressure), a reflux ratio of 10.

The ethyl benzene tower was operated under the condition of a top temperature of 105 degrees centigrade, a top pressure of 40 KPa (gage pressure), a plate number of 95, a bottom temperature of 120 degrees centigrade, a bottom pressure of 55 KPa (gage pressure), a reflux ratio of 10.

The styrene tower was operated under the condition of a top temperature of 80 degrees centigrade, a top pressure of 10 KPa (gage pressure), a plate number of 25, a bottom temperature of 100 degrees centigrade, a bottom pressure of 20 KPa (gage pressure), a reflux ratio of 4.

The reaction was conducted for 20 h, showing that the utilization ratio of the alkylating agent was 37.8%, and the overall selectivity to the alkylate was 97.2%.

Comparative Application Example 1

Methanol is fed by one single step and reacted in one staged reaction zone, wherein the catalyst C-1 was used as the catalyst. In the reaction zone, the reaction temperature was 415 degrees centigrade, the weight hourly space velocity (WHSV) was 2.85 $h^{-1}$, the ratio by molar of toluene to methanol in the feed was 4.5:1, the reaction pressure was 0.1 MPa (gage pressure). The reaction was conducted for 20 h, showing that the utilization ratio of the alkylating agent was 35.4%, and the overall selectivity to the alkylate was 97.4%.

Comparative Application Example 2

Methanol is fed by one single step and reacted in one staged reaction zone, wherein the catalyst C-1 was used as the catalyst. In the reaction zone, the reaction temperature was 400 degrees centigrade, the weight hourly space velocity (WHSV) was 2.65 $h^{-1}$, the ratio by molar of toluene to methanol in the feed was 4.5:1, the reaction pressure was 0.1 MPa (gage pressure). The reaction was conducted for 20 h, showing that the utilization ratio of the alkylating agent was 32.5%, and the overall selectivity to the alkylate was 97.8%.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. An alkylating process for alkyl benzenes to prepare an alkylate, including the following steps:
   a) an alkyl benzene having the following formula (I) and a first stream of alkylating agent being fed into a first reaction zone, contacting with a catalyst A, to produce a process stream I, wherein the alkylating agent is at least one selected from the group consisting of methanol, formaldehyde and dimethoxy methane,

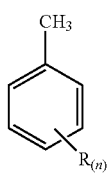

wherein, substituents Rs, when more than one exists, may be the same as or different from one another, each independently selected from the group consisting of $C_{1-4}$ linear or branched alkyls, n represents the number of the substituent R and is an integer of 0, 1 or 2;

b) the process stream I and a second stream of alkylating agent being fed into at least one second reaction zone, contacting with a catalyst B, to produce a process stream II; and c) the process stream II being fed into at least one third reaction zone, contacting with a catalyst C, to produce a process stream III containing an alkylate, wherein a reaction temperature in the first reaction zone is less than a reaction temperature in the third reaction zone, wherein at least one of the catalyst A, the catalyst B and the catalyst C is an alkali metal ion exchanged molecular sieve produced in line with a process including a step of contacting a molecular sieve with an alkali metal ion source to conduct ion-exchanging, wherein the molecular sieve is one or more selected from the group consisting of a X molecular sieve and a Y molecular sieve, and the alkali metal is a combination of K/Rb, a combination of K/Cs, a combination of Rb/Cs or a combination of K/Rb/Cs, wherein the reaction temperature in the first reaction zone is 320-385 degrees centigrade, a reaction temperature in the second reaction zone is 380-420 degrees centigrade, and the reaction temperature in the third reaction zone is 400-450 degrees centigrade, and wherein the alkylate is a compound having the following formula (II) and/or a compound having the following formula (III),

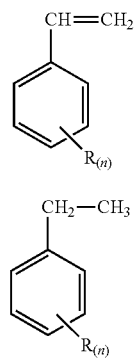

wherein R and n in each formula (II) and (III) are as defined in the formula (I), respectively.

2. The alkylating process according to claim 1, wherein in the first reaction zone, the weight hourly space velocity (WHSV) is 2-4 $h^{-1}$, the reaction pressure is 0-0.5 MPa (gage pressure); in the second reaction zone, the weight hourly space velocity (WHSV) is 2-4 $h^{-1}$, the reaction pressure is 0-0.5 MPa (gage pressure); in the third reaction zone, the weight hourly space velocity (WHSV) is 2-4 $h^{-1}$, the reaction pressure is 0-0.5 MPa (gage pressure); the ratio by molar of the alkyl benzene to the first stream of alkylating agent is greater than 1 but not greater than 6, and the ratio by molar of the alkyl benzene contained in the process stream I to the second stream of alkylating agent is 1-5.

3. The alkylating process according to claim 2, wherein the ratio by molar of the alkyl benzene to the first stream of alkylating agent is greater than the ratio by molar of the alkyl benzene contained in the process stream I to the second stream of alkylating agent.

4. The alkylating process according to claim 2, wherein the ratio by molar of the alkyl benzene to the first stream of alkylating agent is 3.5-5.5; or the ratio by molar of the alkyl benzene contained in the process stream I to the second stream of alkylating agent is 3-5.

5. The alkylating process according to claim 2, wherein the ratio by molar of the alkyl benzene to the first stream of alkylating agent is 3.5-5.5, and the ratio by molar of the alkyl benzene contained in the process stream I to the second stream of alkylating agent is 3-5.

6. The alkylating process according to claim 1, wherein said at least one second reaction zone includes one fixed-bed reactor or two to five serially-connected fixed-bed reactors, said at least one third reaction zone includes one fixed-bed reactor or two to five serially-connected fixed-bed reactors.

7. The alkylating process according to claim 1, wherein the molecular sieve is one or more selected from the group consisting of a X molecular sieve having a ratio of $SiO_2/Al_2O_3$ of 1-7 and a Y molecular sieve having a ratio of $SiO_2/Al_2O_3$ of 1-7, the alkali metal is a combination of K/Rb wherein K and Rb are contained in the catalyst with a content of 0.4-0.8 mmol/g and 2.5-3.1 mmol/g, respectively, a combination of K/Cs wherein K and Cs are contained in the catalyst with a content of 0.7-1.3 mmol/g and 1.8-2.5 mmol/g, respectively, a combination of Rb/Cs wherein Rb and Cs are contained in the catalyst with a content of 0.8-1.5 mmol/g and 1.0-1.7 mmol/g, respectively, or a combination of K/Rb/Cs wherein K, Rb and Cs are contained in the catalyst with a content of 0.4-0.9 mmol/g, 0.5-1.0 mmol/g and 1.8-2.5 mmol/g, respectively.

8. The alkylating process according to claim 7, wherein the X molecular sieve has a ratio of $SiO_2/Al_2O_3$ of 2-3, the combination of K/Rb has a content of K: 0.5-0.7 mmol/g and Rb: 2.8-3.0 mmol/g respectively, the combination of K/Cs has a content of K: 0.8-1.2 mmol/g and Cs: 2.0-2.3 mmol/g respectively, the combination of Rb/Cs has a content of Rb: 1.1-1.4 mmol/g and Cs: 1.3-1.5 mmol/g respectively, or the combination of K/Rb/Cs has a content of K: 0.5-0.7 mmol/g, Rb: 0.6-0.8 mmol/g and Cs: 2.0-2.4 mmol/g respectively.

9. The alkylating process according to claim 7, wherein the alkali metal is a combination of K/Rb/Cs.

10. The alkylating process according to claim 9, wherein the combination of K/Rb/Cs has a content of K: 0.5-0.7 mmol/g, Rb: 0.6-0.8 mmol/g and Cs: 2.0-2.4 mmol/g respectively.

11. The alkylating process according to claim 9, wherein the combination of K/Rb/Cs has a content of K: 0.6-0.7 mmol/g, Rb: 0.7-0.8 mmol/g, Cs: 2.1-2.3 mmol/g respectively.

12. The alkylating process according to claim 7, wherein the alkali metal is a combination of K/Rb wherein K: 0.5-0.7 mmol/g, Rb: 2.8-3.0 mmol/g, a combination of K/Cs wherein K: 0.8-1.2 mmol/g, Cs: 2.0-2.3 mmol/g, a combination of 35 Rb/Cs wherein Rb: 1.1-1.4 mmol/g, Cs: 1.3-1.5 mmol/g or a combination of K/Rb/Cs wherein K: 0.5-0.7 mmol/g, Rb: 0.6-0.8 mmol/g, Cs: 2.0-2.4 mmol/g.

13. The alkylating process according to claim 1, wherein the alkali metal is a combination of K/Rb/Cs, and the contacting includes bringing the molecular sieve into contact with a K ion source, a Rb ion source and a Cs ion source sequentially.

14. The alkylating process according to claim 13, wherein the X molecular sieve has a ratio of $SiO_2/Al_2O_3$ of 1-7, the Y molecular sieve has a ratio of $SiO_2/Al_2O_3$ of 1-7, the combination of K/Rb has a content of K: 0.4-0.8 mmol/g and Rb: 2.5-3.1 mmol/g respectively, the combination of K/Cs has a content of K: 0.7-1.3 mmol/g and Cs: 1.8-2.5 mmol/g respectively, the combination of Rb/Cs has a content of Rb: 0.8-1.5 mmol/g and Cs: 1.0-1.7 mmol/g respectively, or the combination of K/Rb/Cs has a content of K: 0.4-0.9 mmol/g, Rb: 0.5-1.0 mmol/g and Cs: 1.8-2.5 mmol/g respectively.

15. The alkylating process according to claim 13, wherein the combination of K/Rb/Cs has a content of K: 0.5-0.7 mmol/g, Rb: 0.6-0.8 mmol/g and Cs: 2.0-2.4 mmol/g respectively.

16. The alkylating process according to claim 13, wherein the combination of K/Rb/Cs has a content of K: 0.6-0.7 mmol/g, Rb: 0.7-0.8 mmol/g, Cs: 2.1-2.3 mmol/g respectively.

17. The alkylating process according to claim 1, further including the following steps:

d) condensing the process stream III, to obtain a process stream IV, and a vapor stream V containing CO and $H_2$;

e) separating the process stream IV, to obtain an aqueous phase stream and an oil phase stream VI; and f) separating the oil phase stream VI, to obtain an alkyl benzene and the alkylate.

18. The alkylating process according to claim 17, wherein the alkyl benzene obtained from the step f) is recycled to the step a) and/or the step b).

19. The alkylating process according to claim 1, wherein Rs are methyl, or n represents 0.

* * * * *